(12) United States Patent
Machida et al.

(10) Patent No.: US 6,732,778 B1
(45) Date of Patent: May 11, 2004

(54) PRODUCTION METHOD FOR ABSORBENT ARTICLE

(75) Inventors: Yoshinobu Machida, Tochigi (JP); Makoto Kokubo, Tochigi (JP)

(73) Assignee: Kao Corporation, Tokyo (JP)

( * ) Notice: Subject to any disclaimer, the term of this patent is extended or adjusted under 35 U.S.C. 154(b) by 36 days.

(21) Appl. No.: 09/889,847

(22) PCT Filed: Jun. 26, 2000

(86) PCT No.: PCT/JP00/04186

§ 371 (c)(1),
(2), (4) Date: Jul. 23, 2001

(87) PCT Pub. No.: WO01/05345

PCT Pub. Date: Jan. 25, 2001

(30) Foreign Application Priority Data

Jul. 19, 1999 (JP) ............................................. 11-205319

(51) Int. Cl.[7] .............................................. B32B 31/00
(52) U.S. Cl. ....................... 156/361; 156/387; 156/519; 156/494; 156/495; 156/229; 156/264; 156/265; 156/270; 156/164; 156/277; 156/552
(58) Field of Search ................................. 156/351, 361, 156/269, 516, 229, 494, 495, 387, 519, 264, 265, 270, 164, 277, 552

(56) References Cited

U.S. PATENT DOCUMENTS

| | | | |
|---|---|---|---|
| 4,323,069 A | 4/1982 | Ahr et al. | .................... 128/287 |
| 5,045,135 A | 9/1991 | Meissner et al. | .............. 156/64 |
| 5,458,590 A | 10/1995 | Schleinz et al. | ............. 604/361 |
| 5,766,389 A * | 6/1998 | Brandon et al. | ............... 156/64 |

FOREIGN PATENT DOCUMENTS

| | | |
|---|---|---|
| JP | 57-089861 | 6/1982 |
| JP | 63-238861 | 10/1988 |
| JP | 03-090602 | 4/1991 |
| JP | 05-031136 | 2/1993 |
| JP | 2616999 | 3/1997 |
| WO | WO97/24094 A1 | 7/1997 |
| WO | WO98/21035 A1 | 5/1998 |

* cited by examiner

*Primary Examiner*—Linda L. Gray
(74) *Attorney, Agent, or Firm*—Birch, Stewart, Kolasch & Birch, LLP

(57) ABSTRACT

A method for manufacturing an absorbent article comprising the steps of continuously feeding out a long, extensible, continuous member (5) from a predetermined position, cutting the continuous member (5) into lengths (P1) each equivalent to a length of one sheet of the absorbent article at a predetermined position, and fixedly arranging the cut continuous member at a predetermined position of the absorbent article, wherein a predetermined pattern is preliminarily printed on the continuous member (5) at a printing pitch shorter than the cutting length (P1) of the continuous member, and the speed for feeding out is controlled such that the predetermined pattern is located at a predetermined part of the cut continuous member, thereby obtaining the absorbent article in which the predetermined pattern is arranged at a predetermined position.

3 Claims, 3 Drawing Sheets

PRODUCTION METHOD FOR ABSORBENT ARTICLE

This application is the national phase under 35 U.S.C. § 371 of PCT International Application No. PCT/JP00/04186 which has an International filing date of Jun. 26, 2000, which designated the United States of America and was not published in English.

TECHNICAL FIELD

This invention relates to a method for manufacturing an absorbent article with a predetermined pattern arranged at a predetermined position thereof

BACKGROUND ART

Absorbent articles such as disposable diapers are occasionally provided at a predetermined position thereof with a predetermined pattern for the purpose of easy front and rear discrimination. For example, shorts-type diapers for use of children which are manufactured through a cross-flow processing method are occasionally provided at a rear body part thereof with a pattern continuously formed in a widthwise direction or at a central area of a rear body part thereof with a one-point pattern for the purpose of easy front and rear discrimination. Such a pattern is formed by applying a coloring to an elastic member at a waist part, by marking a waist part, or by adhering a colored string to a waist part. In general, front and rear are discriminated by applying a printing pattern to a material of shorts-type diapers and such a pattern has been beloved by mothers and children. As a pattern for diapers for use of children, an animal picture, a vehicle picture, a letter, a food and the like are favorably accepted.

As a technique for continuously producing disposable diapers, there is one which is disclosed in U.S. Pat. No. 5,045,135. As a technique for applying a pattern to a diaper, there is also one which is disclosed in Japanese Pat. No. 2616999.

Conventionally, there has been known a technique, as a technique for applying a predetermined pattern to a predetermined position of a diaper, in which an in-line printing machine is arranged at a midway of a manufacturing line, a pattern is printed on a forming material of an absorbent article such as a leak-preventive sheet in line, and the forming material with a pattern printed thereon is arranged at a predetermined position of the absorbent article. However, such a method is liable to contaminate the manufacturing line. Moreover, in the case where there are a plurality of manufacturing lines, a printing machine is necessary for each manufacturing line and therefore, the cost for the pattern printing is increased. In addition, in the case where a multicolor is to be printed, that number of plates and printing facilities which corresponds to the number of colors become necessary. Thus, many days are required to employ such facilities and in addition, such printing facilities are expensive. In the case where printing is to be changed, not only much expense is required in accordance with the number of lines and plates but also many days are required for employing that number of printing facilities, etc. Moreover, in the case where a solvent-based printing ink is used, ambient air is deteriorated. In the case where a drying process is employed, the line length becomes extremely long. Although there is a printing apparatus using an ink jet, the printing quality is degraded when printing is made at a high speed and positional alignment is extremely difficult in multicolor printing.

In general, a sheet such as film, nonwoven fabric, paper, elastomer and the like onto which a printing is preliminarily applied at constant pitches is difficult to be taken up at a uniform tension from a winding outer part to a winding tail part at the time of taking up a raw sheet into a roll form. Due to non-uniform tension, printing pitch varies when the sheet is fed out from the taken-up roll. Accordingly, when attempt is made to apply a pattern onto the absorbent article using such a sheet, variation of pitch at the time of feeding out the sheet must be corrected in order to make the printing position of the sheet in alignment with the predetermined position of the absorbent article. That is to say, since the printing pitch of the sheet fed out is non-uniform, the feeding amount of the sheet must be changed by increasing or decreasing the speed for feeding out the sheet. However, if the sheet should be overly fed out at that time, tension of the sheet would become zero and sagging and wrinkling (vertical, horizontal and oblique) would occur to the sheet, thereby causing the sheet to travel in a zigzag course. Making the sheet tension zero resulted in degraded product and trouble of a manufacturing line. That is to say, it was conventionally extremely difficult to apply a pattern to a predetermined position of the absorbent article using a sheet with a pattern preliminarily printed thereon.

DISCLOSURE OF INVENTION

It is, therefore, an object of the present invention to provide a method for manufacturing an absorbent article, in which an absorbent article with a predetermined pattern arranged at a predetermined position can be manufactured efficiently, economically and in a stable manner without producing a degraded product.

The present invention has achieved the above object by providing a method for manufacturing an absorbent article comprising the steps of continuously feeding out a long, extensible, continuous member from a predetermined position and conveying, cutting the continuous member into lengths each equivalent to a length of one sheet of the absorbent article at a predetermined position in a conveying path, and fixedly arranging the cut continuous member at a predetermined position of the absorbent article, wherein a predetermined pattern is preliminarily printed on the continuous member at a printing pitch shorter than the cutting length of the continuous member, and the speed for feeding out the continuous member is controlled such that the predetermined pattern is located at a predetermined part of the cut continuous member, thereby obtaining the absorbent article in which the predetermined pattern is arranged at a predetermined position. The expression "extensible" used herein refers to extension in the longitudinal direction, and the expression "cut continuous member" refers to the individual members produced as a result of cutting the continuous member. More preferably, the continuous member is elastically extensible.

Moreover, the present invention provides a long, continuous member preferably used in the above-mentioned method for manufacturing an absorbent article, i.e., which is joined with other members and cut into product lengths each equivalent to a length of one sheet of the absorbent article, together with the other sheet, so as to be used as a part of an absorbent article, wherein patterns are printed on the continuous member in a longitudinal direction thereof at a pitch shorter than the product length, and the printing pitch of the patterns can be made coincident with the product length by extending the continuous member in the longitudinal direction in any step up to the joint with the other members

BEST MODE FOR CARRYING OUT THE INVENTION

Figure 1:
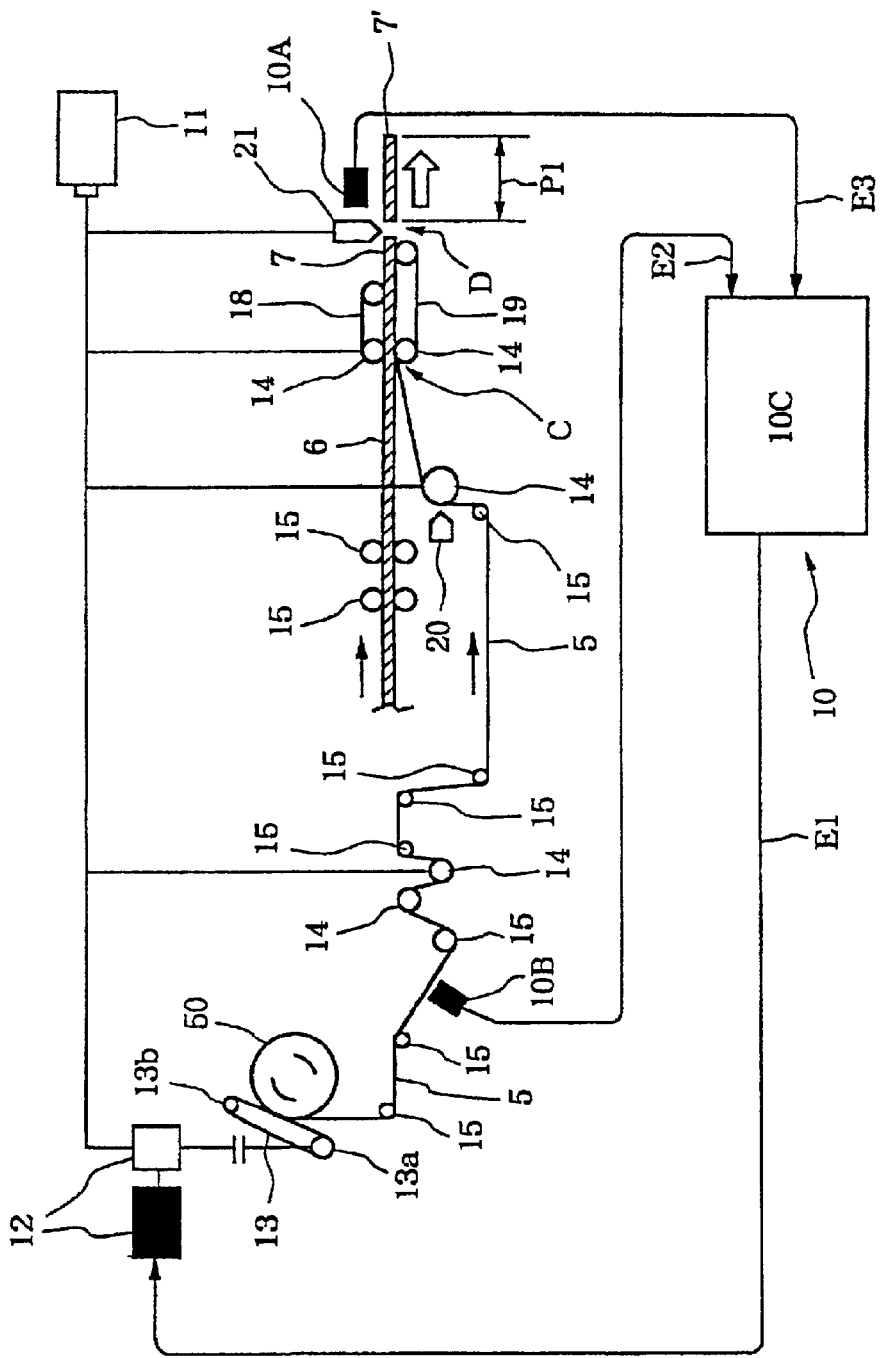
FIG. 1 is a schematic view schematically showing one embodiment of a method for manufacturing an absorbent article according to the present invention together with an apparatus used for carrying out the method.

The present invention will now be described in the form of one preferred embodiment with reference to the drawings. A manufacturing method of this embodiment is a method for manufacturing a disposable diaper 1, in which a non-continuous pattern 4 such as a figure of an animal is arranged on a non-skin contacting surface side of a back side portion A which is located on a wearer's back side when in wear.

First, a disposable diaper manufactured by the present method will be described briefly. A disposable diaper 1 shown in FIG. 2(a) is a so-called flat-type disposable diaper. This disposable diaper 1 comprises a absorptive main body 2 including a liquid-permeable topsheet, a liquid-impermeable back sheet and a liquid-retentive absorbent core interposed therebetween, and an outer layer sheet 3 including a fastening tape (not shown) which is disposed at opposite side edge parts of the back side A which is located on a wearer's back side. The outer layer is arranged at a non-skin contacting surface side of the absorptive main body 2.

A non-continuous pattern 4 is arranged at a central part on the non-skin contacting surface side of the back side portion A in the disposable diaper 1. The pattern 4 is printed on a backsheet 22 forming a surface of the absorptive main body 2 on the non-skin contacting surface side such that the pattern 4 can see through from the top of the outer layer sheet 3 which is disposed in such a manner as to cover the backsheet 22. The pattern 4 is printed on an area in the vicinity of one end part of the vertically elongated backsheet 22. The backsheet 22 is arranged along a direction for connecting the back surface portion A and a stomach side portion B which is located at the wearer's stomach side when in wear, so that the pattern 4 is arranged on the back side portion A.

In the present invention, the expression "pattern is arranged" refers not only to a pattern being printed directly on the outer surface of the absorbent article but also to a pattern being printed on an inside member and which pattern being seen through from outside. In other words, it is good enough if a pattern is disposed such that it can be recognized from outside. Moreover, the term "printing" refers not only to those which belong to printing in its narrow sense such as photo gravure and flexography but also to those in which a pattern is produced by applying physical or chemical treatment to a sheet member. Moreover, it includes not only a pattern which can be recognized visually but also those in which a physical or functional pattern is applied to a sheet member such as partial hydrophilic/water-repellent treatment, opening machining in a very small pattern, for example. Moreover, the expression "non-continuous pattern" refers to a producer's intended pattern being printed on a prescribed position for each product. It should be noted that in FIG. 2, the contour of the absorptive main body 2, which is covered with the outer layer sheet 3 and, therefore, not easily recognized from outside, is indicated by a solid line in an exaggerated manner for the sake of convenience.

An apparatus used for carrying out the method according to this embodiment will be described next. An apparatus shown in FIG. 1 comprises a first sheet member 5 feed-out mechanism for continuously feeding out a first sheet member as the long, extensible continuous member from a predetermined position, a first conveyor mechanism for conveying the first sheet member 5 fed out from the feed-out mechanism to a converging part C where the first sheet member 5 is converged with a second member 6, a second conveying mechanism for conveying a second member 6 as the other continuous member to the converging part C separately from the first sheet member 5, an integrating mechanism for forming a long composite material 7 by integrally joining the first sheet member 5 with the second member 6 thus converged, a cutting mechanism for cutting the composite material 7 into a length which is equivalent to one sheet of absorbent article at a cutting part D located at a predetermined position in a flowing direction of the composite material 7, and a control unit 10 for controlling the speed for feeding out the first sheet member 5 from the feed-out mechanism. The expression "lengths each equivalent to a length of one sheet of the absorbent article" refers to the length of a part of the continuous member which is used for one sheet of an absorbent article as a product. The second member is a long sheet material.

The feed-out mechanism comprises a power source 11, a differential device 12, a feed-out belt 13, etc. In the feed-out mechanism, a sheet of rolled form 50 is rotated by frictional engagement of the feed-out belt 13 and the first sheet member 5 is continuously fed out from the sheet of rolled form 50. The speed of rotation of a drive roller 13a rotated by the feed-out belt 13 is adjusted by the differential device 12. The differential device 12 increases/decreases the speed of rotation of the drive roller 13a in response to a control signal E1 which is input therein by the control unit 10. It should be noted, however, that the drive input is not limited to the illustrated drive source 11, differential device 12 and feed-out belt 13. It may be designed such that an independent servo-motor, or the like receives a control signal.

The first and second conveying mechanisms each comprises the drive source 11, the drive rollers 14, guide rollers 15, etc.

The integrating mechanism comprises one pair of endless-type conveyor belts 18, 19 arranged opposite to each other and an application means 20 for applying an adhesive agent to the first sheet member 5 at an upstream side of the converging part C of the first and second members 5, 6. Upper and lower surfaces of the converged first and second members 5, 6 are pinchingly pressed between the carrier belts 18, 19, thereby integrally joining the two sheets. The long composite material 7 thus formed is conveyed further towards the downstream side. The cutting mechanism comprises a cutting member 21 such as a cutter roll which repeats a cyclic motion upon receipt of power from the power source 11. In the cutting mechanism, the long composite material 7 continuously conveyed at a predetermined speed is cut into a predetermined cutting length (one product pitch P1) which is equivalent to one sheet of absorbent article at a predetermined position in the flowing direction of the composite material 7.

The control unit 10 comprises a machine position detecting means 10A for detecting a machine position, a printing position detecting means 10B for detecting a printing position, and a computing unit 10C for carrying out a predetermined computation and outputting a control signal E1 to the differential device 12 based on a result of the computation in order to adjust a position where a printing (pattern) is to be made, i.e., a predetermined position which is preliminarily determined on the cut-off first sheet member 5, with a current position, i.e., position where a printing (pattern) is to be actually made on the cut-off first sheet member 5, in response to detection signals E2, E3 coming from the detecting means 10A, 10B, respectively. The expression "machine position" herein used refers to a position where a predetermined part (for example: a cutting blade of the cutting member 21 or the like) which repeats a cyclic motion in synchronism with a machining process for each sheet product, exists at a predetermined time in the cycle. This machine position is detected in order to watch the cutting length and cutting position of the continuous member. As a method for detecting the machine position, there can be employed a method in which a dog is disposed at a part of the cutting member 21 which repeats a cyclic motion and the machine position is detected by a proximate switch, a method in which an angular detector is disposed at a drive part (a shaft of one rotation/one sheet) of the cutting member 21 and the machine position is detected by the angular detector, or a method in which a machine position is detected by detecting a predetermined position of a product or material. In this embodiment, the angular detector is used as the machine position detecting means 10A. As a method for detecting a printing position, there is a method for directly seeing the printing part through a photo sensor or CCD camera. In this embodiment, the photo sensor is used as the printing position detecting means 10B.

A method for manufacturing the disposable diaper 1 using the apparatus shown in FIG. 1 will be described next. In the manufacturing method according to this embodiment, a long backsheet forming sheet for forming the backsheet 22 is used as the first sheet member 5, and a long absorbent core forming sheet for forming the absorbent core is used as the second member 6. That is, the backsheet 22 is formed by the first sheet member 5 which has been cut, and the absorbent core is formed by the second member 6 which has been cut. In order to manufacture the disposable diaper 1 as shown in FIG. 2(a) with a predetermined pattern 4 being arranged at the predetermined position P, the predetermined patterns 4 are preliminarily printed on the first sheet member 5 at equal intervals at predetermined printing pitches, and a sheet of rolled form 50 comprising rolling the thus obtained first sheet member 5 is used. The printing pitch is a pitch between every adjacent patterns 4. More specifically, the printing pitch refers to a distance between the same positions (or corresponding positions) in every adjacent patterns 4 such as front ends of every adjacent patterns 4. There is no provision of a dancer roll and the length of the conveying path from the position where the first sheet member 5 is fed out to the first sheet member 5 is converged with the second member 6 is fixed to a predetermined length.

If the sheet gets sagging, it is generally difficult to eliminate the wrinkling, zigzag traveling, etc. In contrast, if the sheet is overly extended, it is also difficult to eliminate the wrinkling, zigzag traveling, etc. Accordingly, it is necessary that the sheet is conveyed with a tension within a predetermined range applied thereto. By doing so, it becomes possible to supply a sheet material which has no wrinkling, in which the zigzag traveling can be adjusted and which has no widthwise shrinkage. Thus, a product of a good quality can be manufactured. Accordingly, it is preferred that the printing pitches of the raw sheet material are shorter than the product pitches. The printing pitches are determined by physical properties such as hysteresis and winding tension of the raw sheet material. The printing pitches of the first sheet member 5 is preferably shorter by 0.5 to 50% and more preferably shorter by 0.5 to 10% with respect to the length (same as the product pitches P1) of the first sheet member 5 which has been cut. The printing pitches can be obtained by cutting a part of the first sheet member 5 before use with no load such that the cut-out sheet includes plural patterns and measuring the distance between the corresponding positions in every adjacent patterns. By setting the printing pitches of the first sheet member 5 within the above-mentioned range, the first sheet member 5 can be used in an extended state without allowing it to get sagged all the time and the tension during the processing can be maintained all the time in an optimal condition.

In the manufacturing method according to this embodiment, the speed for feeding out the first sheet member 5 from the sheet of rolled form 50 is controlled such that the first sheet member 5 is cut in its extended state and the predetermined pattern is arranged at the predetermined part of the first sheet member 5 which has been cut. More specifically, the speed for feeding out the first sheet member 5 is set to be lower than the speed at the cutting part D of the first sheet member 5, i.e., the conveying speed of the composite material 7, so that the first sheet member 5 is maintained in its extended state and so that the first sheet member 5 is fed out by a printing pitch part during the time the first sheet member 5 is cut once at the cutting part D. Then, if the predetermined pattern of the first sheet member 5 which has been cut is offset from the predetermined part, the offset amount is corrected.

Even more specifically, the printing position of the first sheet member 5 fed out from the sheet of rolled form 50 by the feed-out belt 13 is detected by a detecting sensor as the printing position detecting means 10B immediately after the first sheet member 5 is fed out. Between the detecting sensor and the converging part C, it is basically considered that no variation of tension occurs and therefore, the printing position is not offset. Then, a difference between the printing position detected by the detecting sensor and the machine position detecting by the detecting sensor as the machine position detecting means 10A is computed at the computing unit 10C. And the speed of the feed-out belt 13 is increased/decreased such that errors are corrected by the differential device 12 at the time of computation of the difference.

In the method according to this embodiment, a difference between the position where a printing is to be made with respect to the machine position and the printing position of the material which is being processed (or machined) is computed, and the differential device 12 is actuated such that the printing position of the material which is being processed is adjusted to the preset position where a printing is to be made.

When the device shown in FIG. 1 is actuated, the first sheet member 5 is continuously fed out from the sheet of rolled form 50 by the feed-out mechanism and the first sheet member 5 thus fed out is conveyed, via the converging part C, to the cutting part D by the first conveying mechanism. The first sheet member 5 is extended in the longitudinal direction at the time of being fed out and conveyed to the cutting part D in its extended state. The long second member 2 is conveyed to the converging part C by the second conveying mechanism and converged with the first sheet member 5 at the converging part C. The converged first and second sheet members 5 and 6 are integrally joined with each other by the integrating mechanism and the composite material 7 with the predetermined patterns 4 which have been positionally aligned at predetermined pitches on a single surface thereof is formed. Then, the composite material 7 is cut into a predetermined cutting length (one product pitch P1) by the cutting mechanism at the cutting part D on the downstream in the flowing direction of the composite material 7. By cutting of the composite material 7, the first sheet member 5 is cut together with the second member.

During operation of this device, the speed for feeding out the first sheet member 5 from the sheet of rolled form 50 is controlled by the control unit 10 as mentioned above. Therefore, the composite material 7', which has been cut at one product pitch P1, has the pattern 4 arranged at the predetermined position in the longitudinal direction of the composite material 7'.

Accordingly, by arranging the composite material 7', which has been cut, at a predetermined part of the disposable diaper, i.e., at a central pat of the outer layer sheet 3 on the skin-contacting surface side in this embodiment, such that the pattern 4 is located at the back side portion A, there can be obtained the disposable diaper 1 in which the predetermined pattern 4 is arranged at the predetermined position P. In this embodiment, the composite material 7', which has been cut, is placed on and joined with a long outer layer sheet forming sheet which has been separately conveyed, and a long topsheet forming sheet is joined with the top thereof. Thereafter, the long sheets are cut into individual product dimension to thereby obtain the disposable diaper 1. Other required members such as a fastening tape, etc. are attached thereto at a proper stage.

Figure 2:
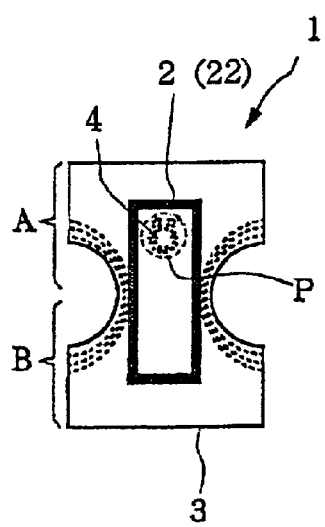
FIG. 2(a) is a view showing one example of an absorbent article which is obtained by the method for manufacturing an absorbent article according to the present invention.
FIGS. 2(b) and 2(c) are views respectively showing examples of an absorbent article with a pattern arranged at a position offset from a predetermined position.
Figure 2:
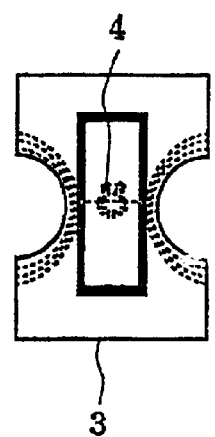
Figure 2:
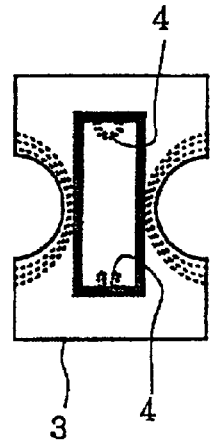

According to the method for manufacturing a disposable diaper of this embodiment, the predetermined pattern 4 can surely be arranged at the targeted predetermined position P and the pattern 4 is never offset from the predetermined position as shown in FIGS. 2(*b*) and 2(*c*). Moreover, since there is no need for arranging the in-line printing machine in the midway of the manufacturing line of the disposable diaper 1, the manufacturing line of a disposable diaper is not complicated. Moreover, since it is possible that the pattern 4 is preliminarily printed on the sheet member 5 at a place different from the manufacturing line of a disposable diaper and this can be brought into the manufacturing line and used, the manufacturing line of a disposable diaper can be prevented from getting contaminated. Moreover, even in the case where a plurality of manufacturing lines are employed, there is no need to provide a printing machine for each manufacturing line. Accordingly, the cost for applying a pattern can be reduced and therefore, there can be manufactured a disposable diaper in an economical manner.

Moreover, by controlling the speed for feeding out the first sheet member 5 in such a manner that the fist sheet member 5 thus fed out is cut in its extended state, the sheet member 5 under conveyance is prevented from getting wrinkling, widthwise variation, travelling in a zigzag course, and the like. Thus, there can be manufactured a disposable diaper having a good quality. Moreover, since the length of the conveying path of the first sheet member 5 from the predetermined position where the first sheet member 5 is fed out to the predetermined position where the first sheet member 5 is cut is fixed to a constant length, the positional alignment of the pattern can be made more easily by controlling the speed for feeding out the first sheet member 5. The first sheet member 5 is one embodiment of the continuous member of the present invention.

Figure 3:
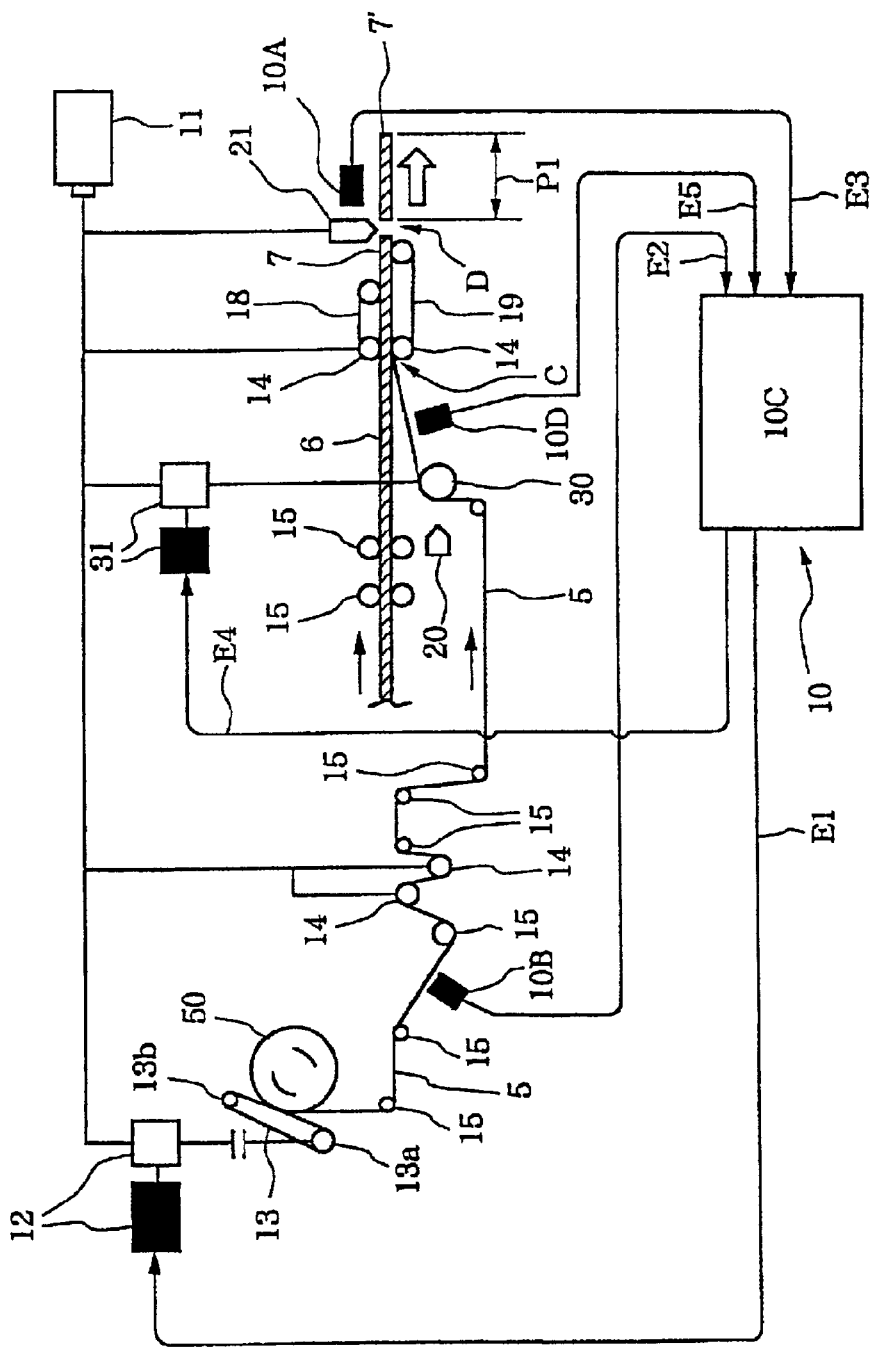
FIG. 3 is a schematic view schematically showing another embodiment of a method for manufacturing an absorbent article according to the present invention together with an apparatus used for carrying out the method.

FIG. 3 shows another embodiment of the present invention. Those points which are different from the embodiment of FIG. 1 are chiefly described and description on similar points thereto is omitted. Description on the above-mentioned embodiment is applied, where appropriate, to those points which are not described in particular. In the embodiment shown in FIG. 3, the first sheet member 5 is fed out from the sheet of rolled form 50 of the first sheet member 5 by the feed-out belt 13, and the feeding amount by the feed-out belt 13 is adjusted while seeing the printing position of the pattern through the first printing position detecting means 10B. Moreover, the printing position is detected by the printing position detecting means 10D at a position immediately before the converging part C, a predetermined computation is made by the computing part 10C in order to make the position where the printing (pattern) is to be made in alignment with the current position in response to the detecting signals E3, E5 coming from the machine position detecting means 10A and the detecting means 10D, respectively. Then, the differential device 31 is actuated by the control signal E4 which is output based on a result of the computation, so that the speed of the driving roll 30 is increased/decreased to make alignment of the printing position. When the distance from the first printing position detecting means 10B to the converging part C is long, it is very effective to add a system in which a positional alignment is made using the additional printing position detecting means 10D and the signal coming from the detecting means 10D. When the process is long, it is effective to introduce a system using a plurality of printing position detecting means and positional aligning means.

The present invention is, by no means, limited to the above-mentioned two embodiments. Instead, it can be changed in accordance with necessity without departing from the subject matter of the present invention.

For example, it is accepted that the first sheet member 5 is cut alone without being joined with the second member and arranged at a predetermined place of the absorbent article. It is also accepted that the second member is not a continuous body but that it is a material which is intermittently fed in. Moreover, the topsheet forming sheet may preliminarily be integrated with the second member 6 as the absorbent core forming sheet. As a material for forming the backsheet 22 (first sheet member 5), the absorbent core (second member 6), the topsheet, the outer layer sheet 3, etc., those, which have heretofore been used for the absorbent article, can be used without any particular limitation. The pattern may include a figure, a letter, a combination of a figure with a letter, and the like. The pattern is also useful for indication of a method for discarding a flat-type or shorts-type disposable diaper or indication of moisture permeability thereof.

The present invention may likewise be applied to a shorts-type disposable diaper, a sanitary napkin, an incontinent pad and the like. It may be used not only for a pattern for discrimination of front and back, but also for indication of a central position and a landing zone, for example, in a disposable diaper, and indication of a brand name and a processing method on a release tape, a packaged film, etc., for example, in a sanitary napkin.

The first sheet member as the continuous member may be joined with the second member as the other continuous member by heat sealing, ultrasonic sealing, or the like. Also, other various kinds of known joining means may be used. As the continuous member on which a pattern is to be printed, various members capable of detecting the position of the printed pattern may be used. Moreover, by joining the continuous member with at least one or more continuous members, for example, a nonwoven fabric partly subjected to hydrophilic/water-repellent treatment, a film/paper/nonwoven fabric provided with a partly large or a plurality of small openings, and a peelable paper or film as the continuous member are subjected to pattern emboss treatment, thereby enabling to manufacture a composite material or the like which is partly provided with irregularities. This makes it possible to manufacture various absorbent articles by using them.

INDUSTRIAL APPLICABILITY

According to the present invention, there can be provided a method for manufacturing an absorbent article in which an absorbent article with a predetermined pattern arranged at a predetermined position thereof can be manufactured efficiently, economically and stably, and without producing any inferior product.

What is claimed is:

1. A method for continuously manufacturing a plurality of absorbent articles comprising the steps of continuously feeding out a long, extensible, continuous member from a predetermined position and conveying, cutting said continuous member into lengths each equivalent to a length of one sheet of said absorbent article at a predetermined position in a conveying path, and fixedly arranging said cut continuous member at a predetermined position of said absorbent article, wherein a predetermined pattern is preliminarily printed on said continuous member at a printing pitch shorter than the cutting length of said continuous member, and the speed for feeding out said continuous member is controlled such that the printing pitch of said patterns at cutting can be made coincident with the cutting length of said continuous member by extending said continuous member in the longitudinal direction, said predetermined pattern is located at a predetermined part of said cut continuous member, said continuous member which is brought into an extended state prior to cut is joined with a continuous absorbent core forming sheet member and optionally at least one other continuous member, and then the joined members are cut altogether, said joined and cut continuous members are arranged together at the predetermined positions of said absorbent article, thereby obtaining the absorbent article in which said predetermined pattern is arranged at each of said predetermined positions.

2. The method for manufacturing an absorbent article according to claim 1, wherein a length of said conveying path of said continuous member from a predetermined position where said continuous member is fed out to a predetermined position where said continuous member is cut is set to a constant length.

3. The method for manufacturing an absorbent article according to claim 1, wherein said at least one other continuous member is selected from the group consisting of: a non-woven fabric partly subjected to hydrophilic or water-repellant repellent treatment; a film or paper or non-woven fabric provided with one or more openings; peelable paper or film; a top sheet; an outer layer sheet; and a fastening tape.

* * * * *